United States Patent
Ahn et al.

(10) Patent No.: US 10,433,370 B2
(45) Date of Patent: Oct. 1, 2019

(54) MICRO MULTI-ARRAY HEATER AND MICRO MULTI-ARRAY SENSOR

(71) Applicant: Point Engineering Co., Ltd., Asan-si, Chungcheongnam-do (KR)

(72) Inventors: Bum Mo Ahn, Suwon-si (KR); Seung Ho Park, Hwaseong-si (KR); Sung Hyun Byun, Hwaseong-si (KR)

(73) Assignee: Point Engineering Co., Ltd., Asan-si, Chungcheongnam-do (KR)

( * ) Notice: Subject to any disclaimer, the term of this patent is extended or adjusted under 35 U.S.C. 154(b) by 46 days.

(21) Appl. No.: 15/634,626

(22) Filed: Jun. 27, 2017

(65) Prior Publication Data
US 2018/0007740 A1    Jan. 4, 2018

(30) Foreign Application Priority Data
Jul. 1, 2016    (KR) .......................... 10-2016-0083417

(51) Int. Cl.
*H05B 1/02* (2006.01)
*H05B 3/00* (2006.01)
(Continued)

(52) U.S. Cl.
CPC ......... *H05B 1/0294* (2013.01); *G01N 27/123* (2013.01); *G01N 27/125* (2013.01);
(Continued)

(58) Field of Classification Search
CPC .. H05B 1/0294; H05B 1/0288; H05B 3/0019; H05B 3/03; H05B 3/16; H05B 6/362; H05B 3/08; H05B 3/26; H05B 220/002; G01N 27/125; G01N 27/128; G01N 27/123
(Continued)

(56) References Cited

U.S. PATENT DOCUMENTS 5,220,140 A * 6/1993 Ball .................. B65D 81/3446
                                                      156/150
6,071,393 A    6/2000 Oshima et al.
(Continued)

FOREIGN PATENT DOCUMENTS

CN    103630575 A    3/2014
CN    104792829 A    7/2015
(Continued)

OTHER PUBLICATIONS

Ahn et al., U.S. Appl. No. 15/634,645 titled "Micro Multi-Array Sensor", filed Jun. 27, 2017, 40 pages.
(Continued)

*Primary Examiner* — Robert R Raevis
(74) *Attorney, Agent, or Firm* — Sunstein Kann Murphy & Timbers LLP (57) ABSTRACT

A micro multi-array heater and a micro multi-array sensor provided with the micro multi-array heater are provided. The micro multi-array heater includes a substrate and a heater electrode formed on the substrate. The heater electrode includes a first heater electrode having a first heat generation pattern and a second heater electrode having a second heat generation pattern. The first heat generation pattern and the second heat generation pattern are formed to have different heat generation amounts.

17 Claims, 6 Drawing Sheets

(51) Int. Cl.
  *G01N 27/12* (2006.01)
  *H05B 3/08* (2006.01)
  *H05B 3/26* (2006.01)
(52) U.S. Cl.
  CPC ......... *G01N 27/128* (2013.01); *H05B 3/0019* (2013.01); *H05B 3/08* (2013.01); *H05B 3/26* (2013.01); *H05B 2203/002* (2013.01)
(58) Field of Classification Search
  USPC ..... 324/94–98; 73/23.2, 24.01, 24.06, 31.01, 73/31.02, 31.05, 31.06, 863.31, 863.11; 422/83, 84, 88, 90, 91
  See application file for complete search history.

(56) References Cited

U.S. PATENT DOCUMENTS

| | | | |
|---|---|---|---|
| 6,350,969 B1* | 2/2002 | Rothchild | C04B 37/021 219/505 |
| 7,861,575 B2 | 1/2011 | Jun et al. | 73/31.06 |
| 8,325,460 B2 | 12/2012 | Park et al. | |
| 8,613,844 B2 | 12/2013 | Ando et al. | |
| 8,680,673 B2 | 3/2014 | Shakar et al. | |
| 10,015,841 B2 | 7/2018 | Ahn et al. | |
| 2002/0118027 A1 | 8/2002 | Routkevitch et al. | |
| 2010/0089902 A1* | 4/2010 | Wong | H05B 3/34 219/387 |
| 2015/0285772 A1 | 10/2015 | Park et al. | |
| 2016/0077044 A1 | 3/2016 | Arkenberg et al. | |
| 2018/0003661 A1 | 1/2018 | Ahn et al. | |

FOREIGN PATENT DOCUMENTS

| | | | |
|---|---|---|---|
| CN | 105445420 A | 3/2016 | |
| EP | 2930500 A1 | 10/2015 | |
| JP | 2012-98232 | 5/2012 | |
| JP | 5630821 B2 | 11/2014 | |
| KR | 10-2006-0094664 A | 8/2006 | |
| KR | 10-2009-0064693 | 6/2009 | ............... B81C 1/00 |
| KR | 10-1019576 | 3/2011 | |
| KR | 10-2012-0048828 | 5/2012 | |
| KR | 10-2015-0071771 | 6/2015 | |
| KR | 10-2016-0035781 A | 4/2016 | |
| KR | 10-2016-0035820 | 4/2016 | |

OTHER PUBLICATIONS

Korean Intellectual Property Office, Office Action—Notification of Grounds for Rejection: Korean Patent Application No. 10-2016-0083417, dated Jul. 18, 2017, 7 pages.

Korean Intellectual Property Office, Office Action—Notification of Grounds for Rejection: Korean Patent Application No. 10-2016-0083417, dated Jul. 18, 2017, 6 pages. (English translation).

Chinese Patent Office, First Examination Report, Application No. 201710513971.X, dated May 13, 2019, 13 pages (including English translation).

* cited by examiner

MICRO MULTI-ARRAY HEATER AND MICRO MULTI-ARRAY SENSOR

CROSS-REFERENCE TO RELATED PATENT APPLICATION

This U.S. non-provisional patent application claims priority under 35 U.S.C. § 119 of Korean Patent Application No. 10-2016-0083417 filed on Jul. 1, 2016 in the Korean Patent Office, the entire contents of which are hereby incorporated by reference.

TECHNICAL FIELD

The present invention relates to a micro multi-array heater and a micro multi-array sensor. More particularly, the present invention pertains to a micro multi-array heater provided with a first heater electrode and a second heater electrode which are different in heat generation amount, and a micro multi-array sensor.

BACKGROUND

As an interest on an environment gradually increases in recent years, a demand has existed for the development of a small-size sensor capable of accurately obtaining different kinds of information within a short period of time. Particularly, for the purpose of making a residential space pleasant, coping with a harmful industrial environment and managing a production process of beverage and foodstuff, efforts have been made to achieve the size reduction, precision enhancement and price reduction of a micro multi-array sensor such as a gas sensor for easily measuring a gas concentration or the like.

The currently available gas sensor gradually evolves from a ceramic-sintered gas sensor or a thick-film-type gas sensor to a micro gas sensor having the form of a micro electro mechanical system (MEMS) due to the application of a semiconductor process technique.

From the viewpoint of a measurement method, a method of measuring a change in the electric characteristics of a sensing material of a sensor when a gas is adsorbed to the sensing material is most frequently used in the currently available gas sensor. Typically, a metal oxide such as $SnO_2$ or the like is used as the sensing material to measure a change in the electrical conductivity depending on the concentration of a measurement target gas. This measurement method has an advantage in that it is relatively easy to use the method. A change in the measurement value becomes conspicuous when the metal oxide sensing material is heated to and operated at a high temperature. Accordingly, accurate temperature control is essential in order to rapidly and accurately measure a gas concentration. Furthermore, the gas concentration is measured after the sensing material is reset or restored to an initial state by forcibly removing gas species or moisture already adsorbed to the sensing material through high-temperature heating.

However, such a conventional sensor is configured to detect one kind of gas. In order to detect plural kinds of gases, there is a need to provide several sensors. This poses a problem in that the volume grows larger and the power consumption increases.

SUMMARY

According to one aspect of the present invention, there is provided a multi-array heater, including: a substrate; and a heater electrode formed on the substrate, wherein the heater electrode includes a first heater electrode having a first heat generation pattern and a second heater electrode having a second heat generation pattern, and the first heat generation pattern and the second heat generation pattern are formed to have different heat generation amounts.

In the micro multi-array heater, the first heat generation pattern and the second heat generation pattern may be connected in parallel.

In the micro multi-array heater, the first heat generation pattern and the second heat generation pattern may be formed to have different lengths.

In the micro multi-array heater, the first heat generation pattern and the second heat generation pattern may be formed to have different thicknesses.

In the micro multi-array heater, at least one air gap disposed between the first heat generation pattern and the second heat generation pattern may be formed in the substrate.

In the micro multi-array, the air gap may include a first air gap surrounding the first heat generation pattern and a second air gap surrounding the second heat generation pattern.

In the micro multi-array heater, the air gap may include a third air gap communicating with the first air gap and the second air gap, and the third air gap may be disposed between the first heat generation pattern and the second heat generation pattern.

In the micro multi-array heater, the air gap may be a space formed to extend from an upper surface of the substrate to a lower surface of the substrate.

In the micro multi-array heater, the substrate may be an anodic oxide film obtained by anodizing a metallic base material and then removing the base material.

In the micro multi-array heater, a dummy metal may be formed on the substrate so as to be disposed between the air gap and the first heat generation pattern or the second heat generation pattern.

According to another aspect of the present invention, there is provided a micro multi-array sensor, including: a substrate; a sensor electrode formed on the substrate; and a heater electrode formed on the substrate, wherein the sensor electrode includes a first sensor electrode having a first sensor wiring and a second sensor electrode having a second sensor wiring, the heater electrode includes a first heater electrode having a first heat generation pattern and a second heater electrode having a second heat generation pattern, the first sensor wiring is disposed more adjacent to the first heat generation pattern than the second heat generation pattern, the second sensor wiring is disposed more adjacent to the second heat generation pattern than the first heat generation pattern, and the first heat generation pattern and the second heat generation pattern are formed to have different heat generation amounts.

In the micro multi-array sensor, the first heat generation pattern and the second heat generation pattern may be connected in parallel.

In the micro multi-array sensor, the first heat generation pattern and the second heat generation pattern may be formed to have different lengths.

In the micro multi-array sensor, the first heat generation pattern and the second heat generation pattern may be formed to have different thicknesses.

In the micro multi-array sensor, at least one air gap disposed between the first heat generation pattern and the second heat generation pattern may be formed in the substrate.

In the micro multi-array sensor, the air gap may include a first air gap surrounding the first heat generation pattern and a second air gap surrounding the second heat generation pattern.

In the micro multi-array sensor, the air gap may include a third air gap communicating with the first air gap and the second air gap, and the third air gap may be disposed between the first heat generation pattern and the second heat generation pattern.

In the micro multi-array sensor, the air gap may be a space formed to extend from an upper surface of the substrate to a lower surface of the substrate.

In the micro multi-array sensor, the substrate may be an anodic oxide film obtained by anodizing a metallic base material and then removing the base material.

In the micro multi-array sensor, a dummy metal may be formed on the substrate so as to be disposed between the air gap and the first heat generation pattern or the second heat generation pattern.

According to the micro multi-array heater and the micro multi-array sensor of the present invention described above, the following effects may be achieved.

The micro multi-array heater is provided with the first heater electrode and the second heater electrode which are different in heat generation amount. By applying the micro multi-array heater to a gas sensor, it is possible to simultaneously detect plural kinds of gases with a simple structure.

The first heat generation pattern and the second heat generation pattern are connected in parallel. The same voltage is applied to the first heat generation pattern and the second heat generation pattern. Thus, the micro multi-array heater may be applied to a product such as a mobile communication device or the like which can be driven at a low voltage and which requires use of low electric power.

The first heat generation pattern and the second heat generation pattern may be formed to have different lengths or to have different thicknesses. Thus, the heat generation amounts of the two heat generation patterns can be made different with a simple structure.

At least one air gap is formed in the substrate and is disposed between the first heat generation pattern and the second heat generation pattern so that the first heat generation pattern and the second heat generation pattern are thermally insulated from each other. Thus, even if two heat generation patterns are formed in one substrate and even if the heat generation temperatures of the two heat generation patterns are made different, it is possible to effectively maintain the respective heat generation temperatures and to accurately detect plural kinds of gases.

The air gap includes the first air gap surrounding the first heat generation pattern and the second air gap surrounding the second heat generation pattern. Thus, the heat capacity is reduced so that a high temperature can be maintained with low electric power.

The air gap further includes a third air gap communicating with the first air gap and the second air gap. The third air gap is disposed between the first heat generation pattern and the second heat generation pattern. This makes it possible to effectively insulate the first heat generation pattern and the second heat generation pattern.

The air gap is a space formed so as to extend from the upper surface of the substrate to the lower surface thereof. This makes it possible to maximize the thermal insulating effect.

The substrate is an anodic oxide film obtained by anodizing a metallic base material and then removing the base material. This makes it possible to further enhance the thermal insulating effect.

The dummy metal is formed on the substrate so as to be disposed between the air gap and the first heat generation pattern or the second heat generation pattern. Thus, the temperature uniformity of the first support portion is improved.

DETAILED DESCRIPTION

Preferred embodiments of the present invention will now be described in detail with reference to the accompanying drawings.

For reference, in the following description, the same configurations of the present invention as those of the related art will not be described in detail. Reference is made to the foregoing description of the related art.

As shown in FIGS. 1 to 4, the micro multi-array sensor provided with a micro multi-array heater of the present embodiment includes a substrate 100, a sensor electrode formed on the substrate 100, and a heater electrode formed on the substrate 100. The sensor electrode includes a first sensor electrode 1300 having a first sensor wiring (pattern) 1310 and a second sensor electrode 2300 having a second sensor wiring (pattern) 2310. The heater electrode includes a first heater electrode 1200 having a first heat generation pattern 1210 and a second heater electrode 2200 having a second heat generation pattern 2210. The first sensor wiring 1310 is disposed more adjacent to the first heat generation pattern 1210 than the second heat generation pattern 2210. The second sensor wiring 2310 is disposed more adjacent to the second heat generation pattern 2210 than the first heat generation pattern 1210. The first heat generation pattern 1210 and the second heat generation pattern 2210 are formed so as to have different heat generation amounts.

If a metallic base material is anodized, there is formed an anodic oxide film including a porous layer having a plurality of pores formed on a surface thereof and a barrier layer existing under the porous layer. In this regard, the metallic base material may be aluminum (Al), titanium (Ti), tungsten (W), zinc (Zn) or the like. It is preferred that the metallic base material is made of aluminum or aluminum alloy which is lightweight, easy to process, superior in heat conductivity and free from contamination of heavy metal.

For example, by anodizing a surface of an aluminum material, it is possible to form an aluminum oxide film including an aluminum oxide porous layer having a plurality of pores 102 formed on a surface thereof and a barrier layer existing under the aluminum oxide porous layer. The substrate 100 according to the preferred embodiment of the present invention may be formed of, for example, only an aluminum oxide film from which aluminum is removed. An electrode may be formed on the aluminum oxide porous layer of the aluminum oxide film. Alternatively, an electrode may be formed on the barrier layer. In addition, the barrier layer of the aluminum oxide film may be removed so that the substrate 100 is formed of only the aluminum oxide porous layer having pores 102 vertically penetrating the substrate 100.

Figure 4:
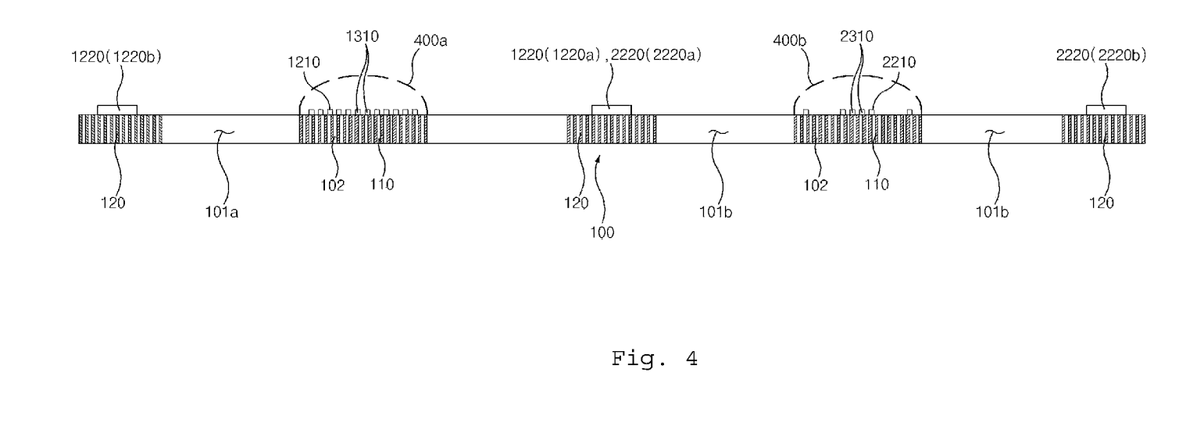
FIG. 4 is a sectional view taken along line C-C in FIG. 1.

The following description will be made based on the substrate 100 from which the aluminum and the barrier layer are removed as shown in FIG. 4.

The aluminum and the barrier layer are removed from the anodized aluminum material. Thus, the pores 102 vertically penetrate the substrate 100. Since the substrate 100 is formed of the aluminum oxide porous layer, the micro multi-array heater has a small heat capacity.

The substrate 100 includes at least two first support portions 110 formed in a cylindrical shape in both side areas of the substrate 100, a second support portion 120 formed outside the first support portions 110 in a spaced-apart relationship with the first support portions 110, and a plurality of bridge portions configured to connect the first support portions 110 and the second support portion 120. A large number of air gaps are formed account the first support portions 110, namely between the first support portions 110 and the second support portion 120. In the present embodiment, two first support portions 110 are formed in one substrate 100. However, the number of the first support portions 110 may be three or more. The respective first support portions 110 are spaced apart from each other.

The air gaps includes first air gaps 101*a* surrounding the periphery of the first support portion 110 disposed on the left side and second air gaps 101*b* surrounding the periphery of the first support portion 110 disposed on the right side.

A large number of air gaps are formed around the first support portions 110. The air gaps may be discontinuously formed. The air gaps and the bridge portions are alternately disposed along the periphery of each of the first support portions 110. The bridge portions are formed by etching the periphery of each of the first support portions 110 and discontinuously forming the air gaps. One ends of the bridge portions are connected to each of the first support portions 110, and the other ends of the bridge portions are connected to the second support portion 120.

Hereinafter, description will be made on the sensor electrode, the heater electrode and a dummy metal 500 formed on the substrate 100.

The sensor electrode is formed on the upper surface of the substrate 100. The sensor electrode detects a gas by detecting a change in electrical characteristic when a gas is adsorbed to a sensing material.

The sensor electrode includes a first sensor electrode 1300 and a second sensor electrode 2300. The first sensor electrode 1300 includes a first sensor wiring 1310 formed on the upper surface of the first support portion 110 disposed on the left side, a bridge portion connected to the first sensor wiring 1310, and a first sensor electrode pad 1320 formed in the second support portion 120.

The first sensor wiring 1310 includes a first sensor wiring first connection portion 1310*a* and a first sensor wiring second connection portion 1310*b*.

The first sensor wiring first connection portion 1310*a* and the first sensor wiring second connection portion 1310*b* are formed in the same shape and are spaced apart from each other in a left-right direction. The first sensor wiring first connection portion 1310*a* and the first sensor wiring second connection portion 1310*b* are formed to linearly extend in an up-down direction.

The first sensor electrode pad 1320 includes a first sensor electrode first pad 1320*a* connected to the first sensor wiring first connection portion 1310*a*, and a first sensor electrode second pad 1320*b* connected to the first sensor wiring second connection portion 1310*b*. The distal end of the first sensor electrode first pad 1320*a* is disposed more adjacent to the first support portion 110 disposed on the right side than the distal end of the first sensor electrode second pad 1320*b*.

The first sensor electrode pad 1320 is formed so as to have a larger width than the first sensor wiring 1310. The first sensor electrode pad 1320 is formed so that the width thereof grows wider toward the distal end thereof.

The first sensor electrode 1300 and the second sensor electrode 2300 are made of one of Pt, W, Co, Ni, Au and Cu or a mixture thereof.

The second sensor electrode 2300 is formed in the same shape as the first sensor electrode 1300. The second sensor electrode 2300 includes a second sensor wiring 2310 formed on the upper surface of the first support portion 110 disposed on the right side, a bridge portion connected to the second sensor wiring 2310, and a second sensor electrode pad 2320 formed in the second support portion 120.

The second sensor wiring 2310 includes a second sensor wiring first connection portion 2310*a*, and a second sensor wiring second connection portion 2310*b*.

The second sensor electrode pad 2320 includes a second sensor electrode first pad 2320*a* connected to the second sensor wiring first connection portion 2310*a*, and a second sensor electrode second pad 2320*b* connected to the second sensor wiring second connection portion 2310*b*. The distal end of the second sensor electrode first pad 2320*a* is disposed more adjacent to the first support portion 110 disposed on the left side than the distal end of the second sensor electrode second pad 2320*b*. The distal end of the second sensor electrode first pad 2320*a* is connected to the distal end of the first sensor electrode first pad 1320*a*.

In the case where the intermediate portion between the second sensor electrode first pad 2320*a* and the first sensor electrode first pad 1320*a* is used as a common electrode, the first sensor electrode 1300 and the second sensor electrode 2300 are connected in parallel.

The heater electrode is formed on the upper surface of the substrate 100.

When the electrodes are formed on the aluminum oxide porous layer of the aluminum oxide film, the upper portions of the pores 102 positioned under the heater electrode and the sensor electrode are closed by the heater electrode and the sensor electrode. The lower portions of the pores 102 are also closed. Alternatively, when the electrodes are formed on the barrier layer of the aluminum oxide film, the upper portions of the pores 102 positioned under the heater electrode and the sensor electrode are closed. The lower portions of the pores 102 are opened. Alternatively, when the barrier layer of the aluminum oxide film is removed, the upper portions of the pores 102 positioned under the heater electrode and the sensor electrode are closed by the heater electrode and the sensor electrode. The lower portions of the pores 102 are opened. In this way, the heater electrode is formed on the aluminum oxide porous layer. This makes it possible to provide a micro multi-array sensor having a small heat capacity.

The heater electrode includes a first heater electrode 1200, and a second heater electrode 2200 spaced apart from the first heater electrode 1200.

The first heater electrode 1200 includes a first heat generation pattern 1210 disposed more adjacent to the first sensor wiring 1310 than the first sensor electrode pad 1320, and a first heater electrode pad 1220 connected to the first heat generation pattern 1210 and formed in the second support portion 120 and the bridge portion.

The first heat generation pattern 1210 is formed on the first support portion 110 disposed on the left side and is formed so as to surround at least a part of the first sensor wiring 1310. The first heater electrode pad 1220 includes a first heater electrode first pad 1220*a* and a first heater electrode second pad 1220*b* respectively connected to both ends of the first heat generation pattern 1210. The first heater electrode first pad 1220*a* and the first heater electrode second pad 1220*b* are spaced apart from each other.

Figure 2:
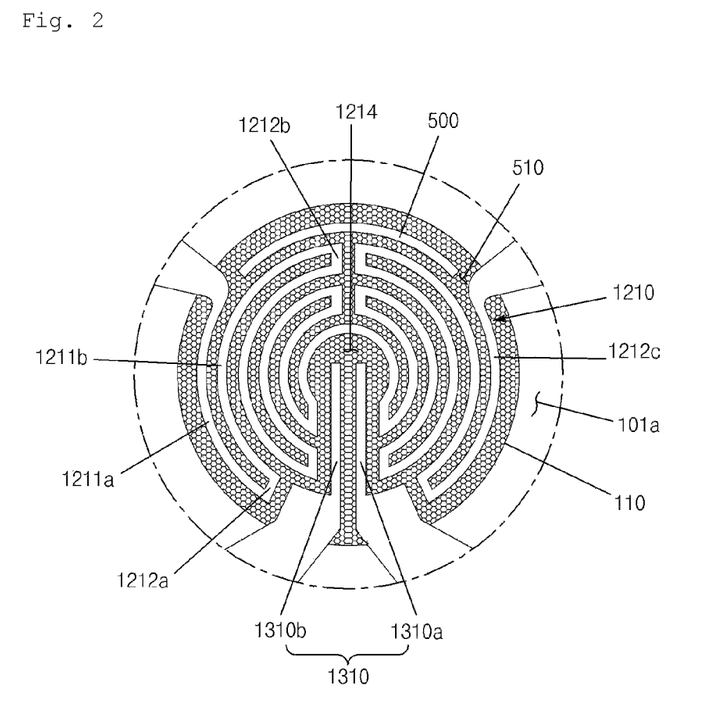
FIG. 2 is an enlarged view of an A region in FIG. 1.

When seen in a plan view as shown in FIG. 2, the first heat generation pattern 1210 includes a plurality of arc portions formed in a circular arc shape so as to be symmetrical with respect to a vertical center axis of the first support portion 110, and a plurality of connection portions configured to connect the arc portions.

The first heat generation pattern 1210 is formed so as to be spaced apart inward from the edge of the first support portion 110.

The first heat generation pattern 1210 includes a first arc portion 1211*a* disposed adjacent to the first air gaps 101*a* and formed in a circular arc shape, a first connection portion 1212*a* bent at one end of the first arc portion 1211*a* so as to extend toward the inner side of the first support portion 110, a second arc portion 1211*b* formed in a circular arc shape so as to extend from an end of the first connection portion 1212*a* and spaced apart inward from the first arc portion 1211*a*, a second connection portion 1212*b* formed so as to extend from an end of the second arc portion 1211*b* toward the inner side of the first support portion 110, a third arc portion 1211*c*, etc. In this way, a plurality of arc portions and a plurality of connection portions are repeatedly connected to each other.

The first heat generation pattern 1210 is integrally formed by connecting the first arc portion 1211*a*, the second arc portion 1211*b* and the third arc portion 1211*c* and is symmetrical with respect to the vertical center axis of the first support portion 110 disposed on the left side.

As shown in FIG. 2, the arc portions of the first heat generation pattern 1210 are formed in a substantially semi-circular arc shape and are symmetrical in a left-right direction. Thus, the first heat generation pattern 1210 forms a substantially circular shape as a whole. This makes it possible to improve the temperature uniformity of the first support portion 110.

Two left and right arc portions meet with each other at the center of the first heat generation pattern 1210. The two arc portions are connected to form a substantially circular shape opened on the lower side. A separation space portion 1214 is formed inside the two arc portions. The separation space portion 1214 is formed so as to extend from the center of the first heat generation pattern 1210 to the lower portion of the first heat generation pattern 1210. That is to say, the left and right arc portions are spaced apart in the left-right direction so that the separation space portion 1214 is formed from the center of the first heat generation pattern 1210 to the lower portion of the first heat generation pattern 1210. The first sensor wiring 1310 is disposed in the separation space portion 1214. Thus, the first heat generation pattern 1210 surrounds the upper portion and the side portions of the first sensor wiring 1310.

The first heater electrode second pad 1220*b* is connected to the other end of the first arc portion 1211*a*. The first heater electrode first pad 1220*a* is connected to one end of the third arc portion 1211*c*.

The first heater electrode 1200 may be made of one of Pt, W, Co, Ni, Au and Cu or a mixture thereof.

Meanwhile, a dummy metal 500 is formed between both ends of the first heat generation pattern 1210, namely between the ends of the first arc portion 1211*a* and the second arc portion 1211*b* to which the first heater electrode first pad 1220*a* and the first heater electrode second pad 1220*b* are respectively connected.

The dummy metal 500 is disposed in a circular arc shape between the first heater electrode 1200, i.e., the first heat generation pattern 1210 and the first air gaps 101*a*. The dummy metal 500 is spaced apart from the first heat generation pattern 1210 adjacent thereto. The dummy metal 500 is spaced apart inward from the edge of the first support portion 110.

It is preferred that the dummy metal 500 is formed outside the first heat generation pattern 1210 and is made of a metal. The material of the dummy metal 500 may be the same as the electrode material. The electrode material may be a metal such as platinum, aluminum, copper or the like.

As shown in FIG. 2, the first arc portion 1211*a* and the third arc portion 1211*c* are shorter in length than the remaining arc portions disposed inside thereof. In the outer periphery of the first heat generation pattern 1210, a space 510 is formed between the ends of the first arc portion 1211*a* and the third arc portion 1211*c*. The dummy metal 500 is positioned in the space 510. The width of the dummy metal 500 is equal to or similar to the width of the first heat generation pattern 1210.

The space 510 existing in the outer periphery of the of the first heat generation pattern 1210 is partially filled with the dummy metal 500. Thus, when seen in a plane view, the outer peripheries of the first heat generation pattern 1210 and the dummy metal 500 form a circle. This makes it possible to improve the temperature uniformity of the first support portion 110.

The first heater electrode first pad 1220*a* and the first heater electrode second pad 1220*b* are formed so that the width thereof grows larger outward. In other words, the first heater electrode pad 1220 is formed so that the width thereof grows smaller toward the first heat generation pattern 1210. The first heater electrode pad 1220 is formed so as to have a larger width than the first heat generation pattern 1210. The first heater electrode first pad 1220*a* is disposed more adjacent to the first support portion 110 disposed on the right side than the first heater electrode second pad 1220*b*.

The second heater electrode 2200 is formed similarly to the first heater electrode 1200. The second heater electrode 2200 includes a second heat generation pattern 2210 disposed more adjacent to the second sensor wiring 2310 than the second sensor electrode pad 2320, and a second heater electrode pad 2220 connected to the first heat generation pattern 1210 and formed in the second support portion 120 and the bridge portion.

The second heat generation pattern 2210 is formed on the first support portion 110 disposed on the right side. Thus, the first sensor wiring 1310 and the first heat generation pattern 1210 are formed on the upper surface of the first support portion 110 disposed on the left side. The second sensor wiring 2310 and the second heat generation pattern 2210 are formed on the upper surface of the first support portion 110 disposed on the right side.

Accordingly, the first sensor wiring 1310 is disposed more adjacent to the first heat generation pattern 1210 than the second heat generation pattern 2210. The second sensor wiring 2310 is disposed more adjacent to the second heat generation pattern 2210 than the first heat generation pattern 1210.

The first heat generation pattern 1210 and the second heat generation pattern 2210 are formed to have different heat generation amounts.

Figure 1:
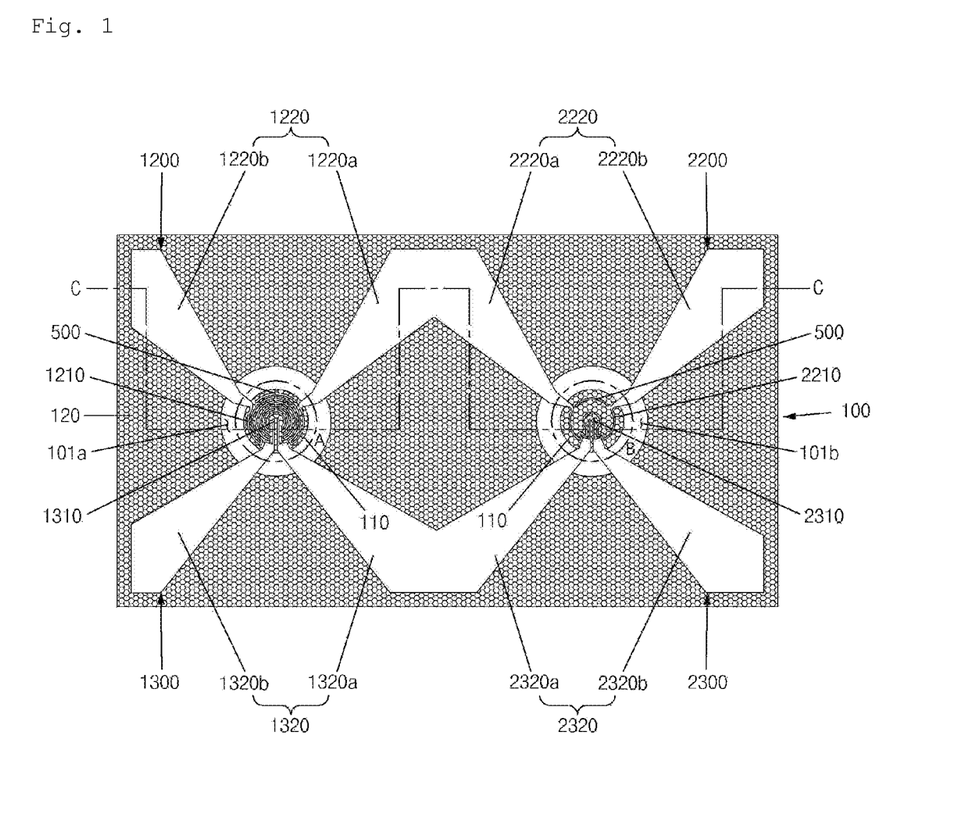
FIG. 1 is a plan view of a micro multi-array sensor provided with a micro multi-array heater according to a preferred embodiment of the present invention.

In order to make the heat generation amounts of the first heat generation pattern 1210 and the second heat generation pattern 2210 different from each other, the first heat generation pattern 1210 and the second heat generation pattern 2210 may be formed to have different lengths as shown in FIG. 1 or may be formed to have different thicknesses.

In the present embodiment, the length of the first heat generation pattern 1210 is larger than the length of the second heat generation pattern 2210 so that a first sensing material 400a formed on the upper surface of the first support portion 110 disposed on the left side can be heated to a higher temperature than a second sensing material 400b formed on the upper surface of the first support portion 110 disposed on the right side. This enables the first sensor electrode 1300 and the second sensor electrode 2300 to detect different kinds of gases.

The first heat generation pattern 1210 is bent to have a smaller gap than the second heat generation pattern 2210. Thus, the first heat generation pattern 1210 and the second heat generation pattern 2210 can be formed in limited areas (first support portions) so as to have different lengths.

Unlike the present embodiment, the first heat generation pattern and the second heat generation pattern may be formed so as not to be symmetrical with respect to the vertical center axis or the horizontal center axis of the first support portion 110. That is to say, the first heat generation pattern and/or the second heat generation pattern may be formed by serially connecting two heat generation patterns bent in a mutually different shape.

The second heat generation pattern 2210 is formed on the first support portion 110 disposed on the right side and is formed so as to surround at least a part of the second sensor wiring 2310. The second heater electrode pad 2220 includes a second heater electrode first pad 2220a and a second heater electrode second pad 2220b respectively connected to both ends of the second heat generation pattern 2210. The second heater electrode first pad 2220a and the second heater electrode second pad 2220b are spaced apart from each other.

Figure 3:
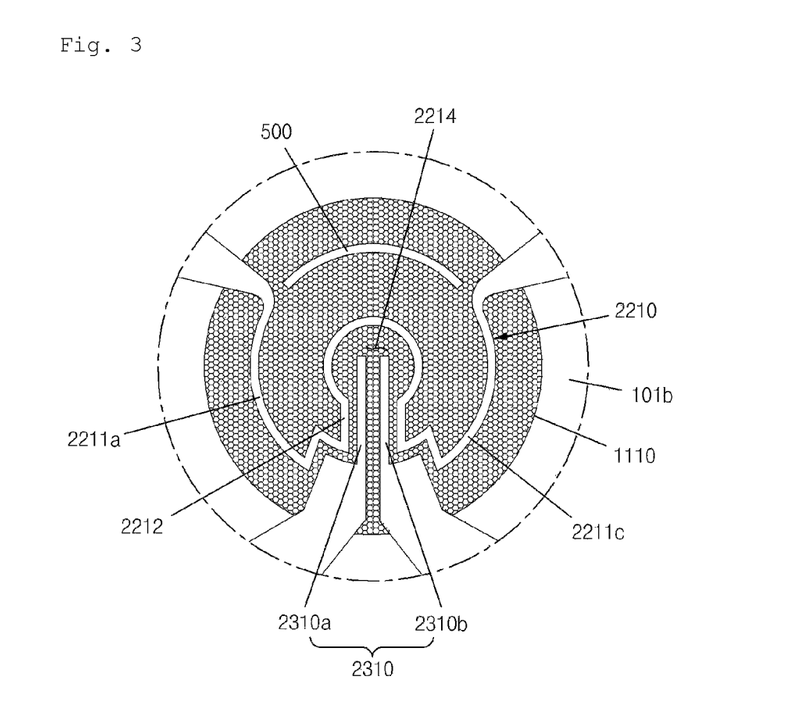
FIG. 3 is an enlarged view of a B region in FIG. 1.

As seen in a plan view as shown in FIG. 3, the second heat generation pattern 2210 is also formed so as to be symmetrical with respect to the vertical center line of the first support portion 110 disposed on the right side.

The second heat generation pattern 2210 is spaced apart inward from the edge of the first support portion 110.

The second heat generation pattern 2210 includes a first arc portion 2211a formed adjacent to the second air gaps 101b so as to have a circular arc shape, a third arc portion 2211c, and a sensor wiring surrounding portion 2212 formed between the first arc portion 2211a and the third arc portion 2211c.

The first arc portion 2211a is connected to the second heater electrode first pad 2220a, and the third arc portion 2211c is connected to the second heater electrode second pad 2220b.

The sensor wiring surrounding portion 2212 is connected to the lower ends of the first arc portion 2211a and the third arc portion 2211c and is formed in a curved shape so as to surround the second sensor wiring 2310. Thus, a separation space portion 2214 with an open lower end is formed in the sensor wiring surrounding portion 2212.

An arc-shape dummy metal 500 is formed between both ends of the second heat generation pattern 2210, namely between the ends of the first arc portion 2211a and the third arc portion 2211c to which the second heater electrode first pad 2220a and the second heater electrode second pad 2220b are respectively connected.

The dummy metal 500 formed on the upper surface of the first support portion 110 disposed on the right side has the same shape and effect as the dummy metal 500 formed on the upper surface of the first support portion 110 disposed on the left side. Thus, the detailed description thereof will be omitted.

In this manner, the dummy metal 500 is formed on the first support portion 110 of the substrate 100 between the first air gaps 101a and the first heat generation pattern 1210, and the dummy metal 500 is formed on the first support portion 110 of the substrate 100 between the second air gaps 101b and the second heat generation pattern 2210.

The second heater electrode first pad 2220a and the second heater electrode second pad 2220b are formed so that the width thereof grows larger outward. That is to say, the second heater electrode pad 2220 is formed so that the width thereof grows smaller toward the second heat generation pattern 2210. The second heater electrode pad 2220 is formed so as to have a larger width than the second heat generation pattern 2210.

The second heater electrode first pad 2220a is disposed more adjacent to the first support portion 110 disposed on the left side than the second heater electrode second pad 2220b.

The second heater electrode first pad 2220a is connected to the first heater electrode first pad 1220a.

In the case where the intermediate portion between the second heater electrode first pad 2220a and the first heater electrode first pad 1220a is used as a common electrode, the first heat generation pattern 1210 and the second heat generation pattern 2210 are connected in parallel.

Alternatively, if electric power is supplied to the first heater electrode 1200 or the second heater electrode 2200 in a state in which the second heater electrode first pad 2220a and the first heater electrode first pad 1220a are merely connected to each other without using the intermediate portion between the second heater electrode first pad 2220a and the first heater electrode first pad 1220a as a common electrode, the first heat generation pattern 1210 and the second heat generation pattern 2210 are connected in series.

As described above, in the heater electrode of the present embodiment, the first heat generation pattern 1210 and the second heat generation pattern 2210 may be connected in parallel or in series depending on the position at which electric power is supplied.

Figure 5:
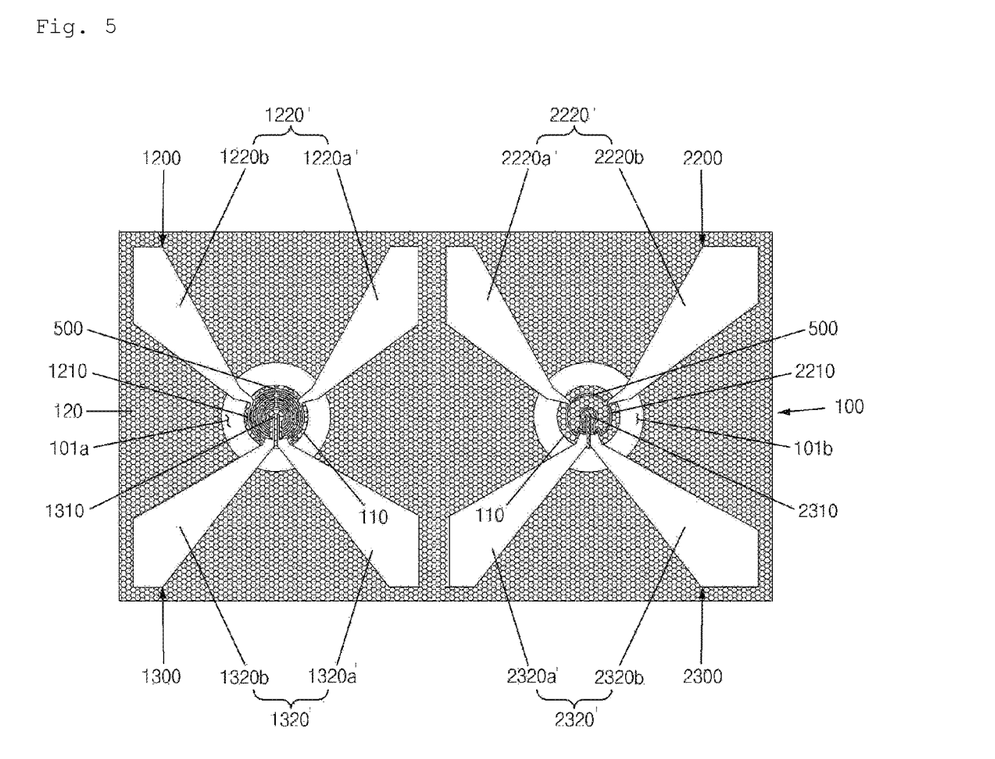
FIG. 5 is a plan view of a micro multi-array sensor provided with a micro multi-array heater according to another preferred embodiment of the present invention.

Unlike the above description, as shown in FIG. 5, the second heater electrode first pad 2220a' and the first heater electrode first pad 1220a' may be formed so as to be separated from each other, and the second sensor electrode first pad 2320a' and the first sensor electrode first pad 1320a' may be formed so as to be separated from each other. When the first and second heater electrode pad 1220' and 2220' and the first and second sensor electrode pads 1320' and 2320' are formed so as to be separated from each other in this manner, it is possible to individually control the left sensor and the right sensor. Therefore, depending on the situations, only the left sensor may be turned on to detect a gas, or only the right sensor may be turned on to detect a gas.

The first and second heater electrode first pads 1220a and 2220a are disposed in the upper middle region of the substrate 100. The first and second heater electrode second pads 1220b and 2220b are disposed in the upper side regions of the substrate 100.

A discoloration-preventing protective layer (not shown) is formed on the entire upper surfaces of the heater electrode and the second sensor electrode. The discoloration-preventing protective layer may be made of an oxide-based material. Specifically, the discoloration-preventing protective layer may be made of at least one of tantalum oxide ($TaO_x$), titanium oxide ($TiO_2$), silicon oxide ($SiO_2$) and aluminum oxide ($Al_2O_3$).

Soldering metals are disposed at the ends of the first and second heater electrode pads 1220 and 2220 and the first and second sensor electrode pads 1320 and 2320. The soldering metals are formed on the discoloration-preventing protective layer. The soldering metals may be at least one of gold, silver and tin.

The first air gaps 101a surround the first heat generation pattern 1210. The second air gaps 101b surround the second heat generation pattern 2210. In this manner, at least one air gap is formed between the first heat generation pattern 1210 and the second heat generation pattern 2210.

The first air gaps 101a and the second air gaps 101b are formed in the same shape. The first air gaps 101a and the second air gaps 101b are formed to have a larger width than the pores 102. Four first air gaps 101a and four second air gaps 101b are formed in a circular arc shape. The first air gaps 101a and the second air gaps 101b are spaced apart in the circumferential direction. That is to say, the first air gaps 101a and the second air gaps 101b are formed discontinuously in a plural number.

Specifically, the first air gaps 101a are disposed between the first sensor electrode second pad 1320b and the first heater electrode second pad 1220b, between the first heater electrode second pad 1220b and the first heater electrode first pad 1220a, between the first heater electrode first pad 1220a and the first sensor electrode first pad 1320a, and between the first sensor electrode first pad 1320a and the first sensor electrode second pad 1320b.

The second air gaps 101b are disposed between the second sensor electrode second pad 2320b and the second heater electrode second pad 2220b, between the second heater electrode second pad 2220b and the second heater electrode first pad 2220a, between the second heater electrode first pad 2220a and the second sensor electrode first pad 2320a, and between the second sensor electrode first pad 2320a and the second sensor electrode second pad 2320b.

In other words, the first air gaps 101a and the second air gaps 101b are formed in the regions other than the portions for supporting the first heater electrode 1200, the second heater electrode 2200, the first sensor electrode 1300 and the second sensor electrode 2300.

The first air gaps 101a and the second air gaps 101b are formed to vertically penetrate the substrate 100. In other words, the first air gaps 101a and the second air gaps 101b are spaces extending from the upper surface of the substrate 100 to the lower surface thereof.

Due to the existence of the first air gaps 101a and the second air gaps 101b, the left first support portion 110 configured to support the first heat generation pattern 1210 and the first sensor wiring 1310, the right first support portion 110 configured to support the second heat generation pattern 2210 and the second sensor wiring 2310, the second support portion 120 configured to support the first heater electrode pad 1220, the second heater electrode pad 2220, the first sensor electrode pad 1320 and the second sensor electrode pad 2320, and the bridge portions are formed in the substrate 100.

Each of the first support portions 110 is formed so as to have a wider area than the total area of the heat generation pattern and the sensor wiring formed on each of the first support portions 110.

The first support portion 110 and the second support portion 120 are spaced apart from each other by the air gaps in the regions other than the bridge portions. In other words, as shown in FIG. 1, the first support portion 110 and the second support portion 120 are connected to each other by the bridge portions at four points.

The second support portion 120 is disposed between the first air gaps 101a and the second air gaps 101b disposed between the left and right first support portions 110. That is to say, the second support portion 120 is disposed between the first air gaps 101a formed between the first heater electrode first pad 1220a and the first sensor electrode first pad 1320a and the second air gaps 101b formed between the second heater electrode first pad 2220a and the second sensor electrode first pad 2320a. Thus, the left first support portion 110, the first air gaps 101a, the second support portion 120, the second air gaps 101b and the right first support portion 110 are sequentially disposed from the left side toward the right side.

Figure 6:
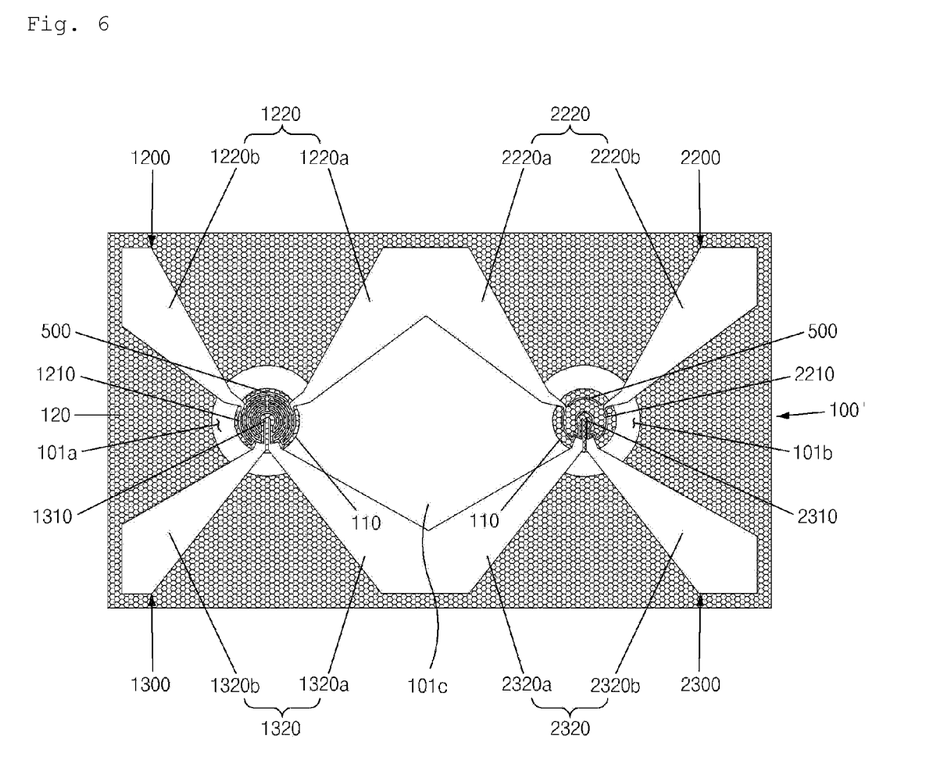
FIG. 6 is a plan view of a micro multi-array sensor provided with a micro multi-array heater according to a further preferred embodiment of the present invention.

Alternatively, as shown in FIG. 6, the air gaps may include a third air gap 101c communicating with the first air gaps 101a and the second air gaps 101b. The third air gap 101c may be disposed between the first heat generation pattern 1210 and the second heat generation pattern 2210. That is to say, the third air gap 101c is disposed between the first air gaps 101a formed between the first heater electrode first pad 1220a and the first sensor electrode first pad 1320a and the second air gaps 101b formed between the second heater electrode first pad 2220a and the second sensor electrode first pad 2320a. Thus, the substrate 100' according to a further embodiment does not have the second support portion 120 in the region between the first air gaps 101a formed between the first heater electrode first pad 1220a and the first sensor electrode first pad 1320a and the second air gaps 101b formed between the second heater electrode first pad 2220a and the second sensor electrode first pad 2320a. Thus, the left first support portion 110, the first air gaps 101a, the third air gap 101c, the second air gaps 101b and the right first support portion 110 are sequentially disposed from the left side toward the right side. The third air gap surrounded by the left first support portion 110, the first heater electrode first pad 1220a, the second heater electrode first pad 2220a, the right first support portion 110, the second sensor electrode first pad 2320a and the first sensor electrode first pad 1320a is formed in the substrate 100'.

A first sensing material 400a and a second sensing material 400b are formed on the first support portions 110, respectively. The first sensing material 400a and the second sensing material 400b are formed at the positions corresponding to the first support portions 110. The first sensing material 400a covers the first heat generation pattern 1210 and the first sensor wiring 1310. The second sensing material 400b covers the second heat generation pattern 2210 and the second sensor wiring 2310.

The first sensing material 400a and the second sensing material 400b may be made of the same material or different materials. Even if the same sensing material is used, different gases may be adsorbed to the sensing material depending on the heating temperature.

The first sensing material 400a and the second sensing material 400b are formed by printing. When the first sensing material 400a and the second sensing material 400b are formed by printing in this manner, a mesh-like mark is left on the surface of each of the first sensing material 400a and the second sensing material 400b after forming the first sensing material 400a and the second sensing material 400b.

The operations of the micro multi-array heater and the micro multi-array sensor according to the present embodiment configured as above will now be described.

In order to measure a gas concentration, first, electric power having the same level is simultaneously applied to the first heater electrode pad 1220 and the second heater electrode pad 2220 so that the first heat generation pattern 1210 and the second heat generation pattern 2210 can generate heat. Since the first heat generation pattern 1210 is longer than the second heat generation pattern 2210, the first sensing material 400a is heated to a higher temperature than the second sensing material 400b.

Thus, different gases are adsorbed to or desorbed from the first sensing material 400a and the second sensing material 400b. Through such a process, the micro multi-array sensor according to the present embodiment can simultaneously detect plural kinds of gases.

While some preferred embodiments of the present invention have been described above, a person skilled in the relevant technical field will be able to differently change or modify the present invention without departing from the spirit and scope of the present invention defined in the claims.

What is claimed is:

1. A multi-array sensor with a multi-array heater comprising:
   a substrate, which is an anodic oxide film including a porous layer, obtained by anodizing a metallic base material and then removing the base material; and
   heater electrodes formed on the substrate, wherein the heater electrodes include a first heater electrode having a first heat generation pattern and a second heater electrode having a second heat generation pattern, and
   the first heat generation pattern and the second heat generation pattern are formed to have different heat generation amounts and different thicknesses.

2. The multi-array sensor with the multi-array heater of claim 1, wherein the first heat generation pattern and the second heat generation pattern are connected in parallel.

3. The multi-array sensor with the multi-array heater of claim 1, wherein the first heat generation pattern and the second heat generation pattern are formed to have different lengths.

4. The multi-array sensor with the multi-array heater of claim 1, wherein at least one air gap disposed between the first heat generation pattern and the second heat generation pattern is formed in the substrate.

5. The multi-array sensor with the multi-array heater of claim 4, wherein the air gap includes a first air gap surrounding the first heat generation pattern and a second air gap surrounding the second heat generation pattern.

6. The multi-array sensor with the multi-array heater of claim 5, wherein the at least one air gap includes a third air gap connecting the first air gap with the second air gap.

7. The multi-array sensor with the multi-array heater of claim 4, wherein the air gap is a space formed to extend from an upper surface of the substrate to a lower surface of the substrate.

8. The multi-array sensor with the multi-array heater of claim 4, wherein a dummy metal is formed on the substrate so as to be disposed between the air gap and the first heat generation pattern or the second heat generation pattern.

9. The multi-array sensor with the multi-array heater of claim 1, further comprising:
   a sensor electrode formed on the substrate; and
   wherein the sensor electrode includes a first sensor electrode having a first sensor wiring and a second sensor electrode having a second sensor wiring,
   the first sensor wiring is disposed more adjacent to the first heat generation pattern than the second heat generation pattern,
   the second sensor wiring is disposed more adjacent to the second heat generation pattern than the first heat generation pattern.

10. The multi-array sensor with the multi-array heater of claim 9, wherein the first heat generation pattern and the second heat generation pattern are connected in parallel.

11. The multi-array sensor with the multi-array heater of claim 9, wherein the first heat generation pattern and the second heat generation pattern are formed to have different lengths.

12. The multi-array sensor with the multi-array heater of claim 9, wherein the first heat generation pattern and the second heat generation pattern are formed to have different thicknesses.

13. The multi-array sensor with the multi-array heater of claim 9, wherein at least one air gap disposed between the first heat generation pattern and the second heat generation pattern is formed in the substrate.

14. The multi-array sensor with the multi-array heater of claim 13, wherein the air gap includes a first air gap surrounding the first heat generation pattern and a second air gap surrounding the second heat generation pattern.

15. The multi-array sensor with the multi-array heater of claim 14, wherein the at least one air gap includes a third air gap connecting the first air gap with the second air gap.

16. The multi-array sensor with the multi-array heater of claim 13, wherein the air gap is a space formed to extend from an upper surface of the substrate to a lower surface of the substrate.

17. The multi-array sensor with the multi-array heater of claim 13, wherein a dummy metal is formed on the substrate so as to be disposed between the air gap and the first heat generation pattern or the second heat generation pattern.

* * * * *